US011612360B2

(12) United States Patent
Averina et al.

(10) Patent No.: US 11,612,360 B2
(45) Date of Patent: Mar. 28, 2023

(54) DISCHARGE READINESS ASSESSMENT

(71) Applicant: Cardiac Pacemakers, Inc., St. Paul, MN (US)

(72) Inventors: Viktoria A. Averina, Shoreview, MN (US); Pramodsingh Hirasingh Thakur, Woodbury, MN (US); Qi An, Blaine, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 49 days.

(21) Appl. No.: 16/241,669

(22) Filed: Jan. 7, 2019

(65) Prior Publication Data

US 2019/0216404 A1 Jul. 18, 2019

Related U.S. Application Data

(60) Provisional application No. 62/617,016, filed on Jan. 12, 2018.

(51) Int. Cl.
*A61B 5/00* (2006.01)
*G16H 40/20* (2018.01)
*G16H 10/60* (2018.01)
*G16H 50/30* (2018.01)
*A61B 5/08* (2006.01)
(Continued)

(52) U.S. Cl.
CPC ........ *A61B 5/7275* (2013.01); *A61B 5/02055* (2013.01); *A61B 5/08* (2013.01); *A61B 5/7282* (2013.01); *G16H 10/60* (2018.01); *G16H 40/20* (2018.01); *G16H 50/30* (2018.01); *A61B 5/0006* (2013.01); *A61B 5/021* (2013.01); *A61B 5/1118* (2013.01); *A61B 5/316* (2021.01); *A61B 5/686* (2013.01)

(58) Field of Classification Search
CPC ..... A61B 5/7275; A61B 5/02055; A61B 5/08; A61B 5/7282; A61B 5/0006; A61B 5/021; A61B 5/04012; A61B 5/1118; A61B 5/686; G16H 40/20; G16H 10/60; G16H 50/30
See application file for complete search history.

(56) References Cited

U.S. PATENT DOCUMENTS 9,622,664 B2 4/2017 An et al.
2008/0228090 A1* 9/2008 Wariar ................. A61B 5/0215
600/508
(Continued)

FOREIGN PATENT DOCUMENTS

WO WO-2019139850 A1 7/2019

OTHER PUBLICATIONS

Caldwell MA, Howie JN, Dracup K. BNP as discharge criteria for heart failure. J Card Fail. Oct. 2003;9(5):416-22. doi: 10.1054/s1071-9164(03)00124-6. PMID: 14583905. (Year: 2003).*
(Continued)

*Primary Examiner* — Gary Jackson
*Assistant Examiner* — Alexander M Eisenberg
(74) *Attorney, Agent, or Firm* — Schwegman Lundberg & Woessner, P.A.

(57) ABSTRACT

This document discusses, among other things, systems and methods to determine an indication of discharge readiness for a patient using received physiologic information of the patient corresponding to hospitalization of the patient and received physiologic information of the patient corresponding to a time after hospitalization.

19 Claims, 4 Drawing Sheets

(51) Int. Cl.
*A61B 5/316* (2021.01)
*A61B 5/021* (2006.01)
*A61B 5/0205* (2006.01)
*A61B 5/11* (2006.01)

(56) References Cited

U.S. PATENT DOCUMENTS

| | | | |
|---|---|---|---|
| 2012/0253207 A1* | 10/2012 | Sarkar | A61B 5/7275 600/483 |
| 2013/0060151 A1 | 3/2013 | Wariar et al. | |
| 2014/0276164 A1* | 9/2014 | Thakur | A61B 5/746 600/528 |
| 2015/0164375 A1* | 6/2015 | Schindhelm | G16H 50/20 600/534 |
| 2015/0302150 A1 | 10/2015 | Mazar et al. | |
| 2015/0305688 A1 | 10/2015 | Rath et al. | |
| 2016/0000380 A1* | 1/2016 | Averina | A61B 5/0537 600/301 |
| 2016/0180029 A1* | 6/2016 | Shanbhag | G16H 10/60 705/3 |
| 2017/0231568 A1* | 8/2017 | An | G16H 40/63 600/301 |
| 2017/0325779 A1* | 11/2017 | Spina | A61B 7/003 |

OTHER PUBLICATIONS

Atienza F et al. Multicenter randomized trial of a comprehensive hospital discharge and outpatient heart failure management program. Eur J Heart Fail. Aug. 2004;6(5):643-52. doi: 10.1016/j.ejhear(Year: 2004).*
Tang WH, Tong W. Measuring impedance in congestive heart failure: current options and clinical applications. Am Heart J. Mar. 2009;157(3):402-11. doi: 10.1016/j.ahj.2008.10.016. Epub Dec. 16, 2008. PMID: 19249408; PMCID: PMC3058607. (Year: 2009).*
Negi S, Sawano M, Kohsaka S, Inohara T, Shiraishi Y, et al. (2014) Prognostic Implication of Physical Signs of Congestion in Acute Heart Failure Patients and Its Association with Steady-State Biomarker Levels. PLOS ONE 9(5): e96325. https://doi.org/10.1371/journal.pone.0096325 (Year: 2014).*
"International Application Serial No. PCT/US2019/012530, International Preliminary Report on Patentability dated Jul. 23, 2020", 8 pgs.
"International Application Serial No. PCT/US2019/012530, International Search Report dated May 3, 2019", 5 pgs.
"International Application Serial No. PCT/US2019/012530, Written Opinion dated May 3, 2019", 9 pgs.
Tang, Wilson W.H., et al., "Measuring impedance in congestive heart failure: Current options and clinical applications", American Heart Journal, vol. 157, No. 3, XP055568283,, (Mar. 1, 2009), 402-411.
"European Application Serial No. 19704900.0, Response filed Mar. 18, 2021 to Communication pursuant to Rules 161(1) and 162 EPC dated Mar. 18, 2021", 34 pgs.

* cited by examiner

DISCHARGE READINESS ASSESSMENT

CLAIM OF PRIORITY

This application claims the benefit of priority under 35 U.S.C. § 119(e) of U.S. Provisional Patent Application Ser. No. 62/617,016, filed on Jan. 12, 2018, which is herein incorporated by reference in its entirety.

TECHNICAL FIELD

This document relates generally to medical devices, and more particularly, but not by way of limitation, to systems, devices, and methods for discharge readiness assessment.

BACKGROUND

Congestive heart failure (CHF) is a reduction in the ability of the heart to deliver enough blood to meet bodily needs, affecting over five million patients in the United States alone. CHF patients commonly have enlarged heart with weakened cardiac muscles, resulting in reduced contractility and poor cardiac output of blood.

CHF is typically a chronic condition, but can also occur suddenly, affecting the left, right, or both sides of a heart. If CHF affects the left ventricle, signals that control the left ventricular contraction can be delayed, causing left ventricular dysfunction, further decreasing the pumping efficiency of the heart.

CHF is one of many conditions that can lead to hospitalization of a patient. CHF and other conditions can be monitored using one or more sensors or ambulatory devices. In an example, an assessment circuit can provide a determination of CHF or risk or stratification of worsening CHF using information from the one or more sensors or ambulatory devices, and an alert or indication can be provided to the patient or a clinician that a patient seek medical treatment or be hospitalized.

SUMMARY

This document discusses, among other things, systems and methods to determine an indication of discharge readiness for a patient using received physiologic information of the patient corresponding to hospitalization of the patient and received physiologic information of the patient corresponding to a time after hospitalization.

An example (e.g., "Example 1") of subject matter (e.g., a system) may include a signal receiver circuit configured to receive physiologic information of a patient; and receive an indication of hospitalization of the patient an assessment circuit configured to: determine an indication of discharge readiness for the patient using: received physiologic information of the patient corresponding to the hospitalization of the patient; and received physiologic information of the patient corresponding to a time after hospitalization.

In Example 2, the subject matter of Example 1 may optionally be configured to include a respiration sensor configured to detect respiration information from the patient and provide a respiration parameter; or a heart sound sensor configured to detect heart sound information from the patient and provide a heart sound parameter, wherein the signal receiver circuit is configured to receive physiologic information of the patient including at least one of the respiration parameter or the heart sound parameter.

In Example 3, the subject matter of any one or more of Examples 1-2 may optionally be configured such that the signal receiver circuit is configured to receive physiologic information of the patient including the respiration parameter and the heart sound parameter.

In Example 4, the subject matter of any one or more of Examples 1-3 may optionally be configured such that the respiration parameter includes at least one of a respiratory rate, a tidal volume, or a rapid shallow breathing index (RSBI) of the patient.

In Example 5, the subject matter of any one or more of Examples 1-4 may optionally be configured such that the heart sound parameter includes at least one of a third heart sound (S3) energy or a first heart sound (S1) amplitude or energy.

In Example 6, the subject matter of any one or more of Examples 1-5 may optionally be configured such that the assessment circuit is configured to determine a congestive heart failure (CHF) parameter using received physiologic information prior to hospitalization of the patient, wherein the CHF parameter prior to hospitalization of the patient is different than the indication of discharge readiness.

In Example 7, the subject matter of any one or more of Examples 1-6 may optionally be configured to include a thoracic impedance sensor configured to detect thoracic impedance information from the patient and provide a thoracic impedance parameter, wherein the signal receiver circuit is configured to receive physiologic information from the patient including the thoracic impedance parameter, and the assessment circuit is configured to determine the CHF parameter using the thoracic impedance parameter of the patient prior to hospitalization, and to determine the indication of discharge readiness using other information not including the thoracic impedance.

In Example 8, the subject matter of any one or more of Examples 1-7 may optionally be configured such that the signal receiver circuit is configured to receive an indication of discharge of the patient from a hospital, and the assessment circuit is configured to determine a rehospitalization parameter using received physiologic information corresponding to a time after discharge of the patient, wherein the rehospitalization parameter is different than the indication of discharge readiness.

In Example 9, the subject matter of any one or more of Examples 1-8 may optionally be configured such that the assessment circuit is configured to provide the determined indication of discharge readiness to a display, and the assessment circuit is configured to determine the indication of discharge readiness for the patient using received physiologic information of the patient corresponding to a time after hospitalization but before discharge of the patient from the hospital.

In Example 10, the subject matter of any one or more of Examples 1-9 may optionally be configured such that the received physiologic information of the patient corresponding to the hospitalization of the patient includes an average daily value of the physiologic parameter at the time of hospitalization, and the received physiologic information of the patient corresponding to a time after hospitalization of the patient includes a current average daily value at the time of determining the indication of discharge readiness.

In Example 11, the subject matter of any one or more of Examples 1-10 may optionally be configured such that the assessment circuit is configured to: determine, at a first time, a first discharge score using received physiologic information of the patient corresponding to the hospitalization of the patient; and determine, at a second time later than the first time, a second discharge score using received physiologic information of the patient corresponding to the time after hospitalization of the patient, wherein the assessment circuit is configured to determine the indication of discharge readiness for the patient using the determined first and second discharge scores.

An example (e.g., "Example 12") of subject matter (e.g., a machine-readable medium) may optionally include instructions that, when performed by a medical device, cause the medical device to: receive physiologic information of a patient; receive an indication of hospitalization of the patient; and determine an indication of discharge readiness for the patient using: received physiologic information of the patient corresponding to the hospitalization of the patient; and received physiologic information of the patient corresponding to a time after hospitalization.

In Example 13, the subject matter of Example 12 may optionally include instructions that, when performed by the medical device, cause the medical device to receive physiologic information of a patient include instructions to: receive physiologic information of the patient including at least one of a respiration parameter or a heart sound parameter.

In Example 14, the subject matter of any one or more of Examples 12-13 may optionally include instructions that, when performed by the medical device, cause the medical device to receive physiologic information of a patient include instructions to: receive an average daily value of the physiologic parameter at the time of hospitalization, and receive a current average daily value at the time of determining the indication of discharge readiness.

In Example 15, the subject matter of any one or more of Examples 12-14 may optionally include instructions that, when performed by the medical device, cause the medical device to determine an indication of discharge readiness for the patient include instructions to: determine, at a first time, a first discharge score using received physiologic information of the patient corresponding to the hospitalization of the patient; determine, at a second time later than the first time, a second discharge score using received physiologic information of the patient corresponding to the time after hospitalization of the patient; and determine the indication of discharge readiness for the patient using the determined first and second discharge scores.

An example (e.g., "Example 16") of subject matter (e.g., a method) may optionally include receiving physiologic information of a patient using a signal receiver circuit; receiving an indication of hospitalization of the patient using the signal receiver circuit; and determining, using an assessment circuit, an indication of discharge readiness for the patient using: received physiologic information of the patient corresponding to the hospitalization of the patient; and received physiologic information of the patient corresponding to a time after hospitalization.

In Example 17, the subject matter of Example 16 may optionally be configured to include detecting respiration information from the patient and providing a respiration parameter using a respiration sensor; and detecting heart sound information from the patient and providing a heart sound parameter using a heart sound sensor, wherein the receiving physiologic information of the patient includes receiving at least one of the respiration parameter or the heart sound parameter.

In Example 18, the subject matter of any one or more of Examples 16-17 may optionally be configured such that the receiving physiologic information of the patient includes: receiving at least one of a respiratory rate, a tidal volume, or a rapid shallow breathing index (RSBI) of the patient, and receiving at least one of a third heart sound (S3) energy or a first heart sound (S1) amplitude or energy.

In Example 19, the subject matter of any one or more of Examples 16-18 may optionally be configured to include determining, using the assessment circuit, a congestive heart failure (CHF) parameter using received physiologic information prior to hospitalization of the patient, wherein the CHF parameter prior to hospitalization of the patient is different than the indication of discharge readiness; receiving an indication of discharge of the patient from a hospital; and determining, using the assessment circuit, a rehospitalization parameter using received physiologic information corresponding to a time after discharge of the patient, wherein the rehospitalization parameter is different than the indication of discharge readiness, wherein the determining the indication of discharge readiness for the patient includes using received physiologic information corresponding to a time after hospitalization but before discharge of the patient from the hospital.

In Example 20, the subject matter of any one or more of Examples 16-19 may optionally be configured such that determining the indication of discharge readiness includes: determining, at a first time, a first discharge score using received physiologic information of the patient corresponding to the hospitalization of the patient; determining, at a second time later than the first time, a second discharge score using received physiologic information of the patient corresponding to the time after hospitalization of the patient; and determining the indication of discharge readiness for the patient using the determined first and second discharge scores.

An example (e.g., "Example 21") of subject matter (e.g., a system or apparatus) may optionally combine any portion or combination of any portion of any one or more of Examples 1-20 to include "means for" performing any portion of any one or more of the functions or methods of Examples 1-20, or a "non-transitory machine-readable medium" including instructions that, when performed by a machine, cause the machine to perform any portion of any one or more of the functions or methods of Examples 1-20.

This summary is intended to provide an overview of subject matter of the present patent application. It is not intended to provide an exclusive or exhaustive explanation of the disclosure. The detailed description is included to provide further information about the present patent application. Other aspects of the disclosure will be apparent to persons skilled in the art upon reading and understanding the following detailed description and viewing the drawings that form a part thereof, each of which are not to be taken in a limiting sense.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Figure 1:
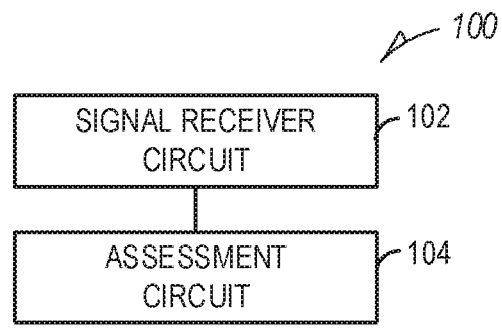
FIG. 1 illustrates an example system including a signal receiver circuit and an assessment circuit.

Ambulatory medical devices, including implantable, leadless, or wearable medical devices configured to monitor, detect, or treat various cardiac conditions resulting in a reduced ability of a heart to sufficiently deliver blood to a body, such as congestive heart failure (CHF). Various ambulatory medical devices can be implanted in a patient's body or otherwise positioned on or about the patient to monitor patient physiologic information, such as heart sounds, respiration (e.g., respiration rate, tidal volume, etc.), impedance (e.g., thoracic impedance), pressure, cardiac activity (e.g., heart rate), physical activity, or one or more other physiologic parameters of a patient, or to provide electrical stimulation or one or more other therapies or treatments to optimize or control contractions of the heart.

Traditional cardiac rhythm management (CRM) devices, such as pacemakers, defibrillators, or cardiac monitors, include subcutaneous devices configured to be implanted in a chest of a patient, having one or more leads to position one or more electrodes or other sensors at various locations in the heart, such as in one or more of the atria or ventricles. Separate from, or in addition to, the one or more electrodes or other sensors of the leads, the CRM device can include one or more electrodes or other sensors (e.g., a pressure sensor, an accelerometer, a gyroscope, a microphone, etc.) powered by a power source in the CRM device. The one or more electrodes or other sensors of the leads, the CRM device, or a combination thereof, can be configured detect physiologic information from, or provide one or more therapies or stimulation to, the patient.

Leadless cardiac pacemakers (LCP) include small (e.g., smaller than traditional implantable CRM devices), self-contained devices configured to detect physiologic information from or provide one or more therapies or stimulation to the heart without traditional lead or implantable CRM device complications (e.g., required incision and pocket, complications associated with lead placement, breakage, or migration, etc.). In certain examples, an LCP can have more limited power and processing capabilities than a traditional CRM device; however, multiple LCP devices can be implanted in or about the heart to detect physiologic information from, or provide one or more therapies or stimulation to, one or more chambers of the heart. The multiple LCP devices can communicate between themselves, or one or more other implanted or external devices.

Wearable or external medical sensors or devices can be configured to detect or monitor physiologic information of the patient without required implant or an in-patient procedure for placement, battery replacement, or repair. However, such sensors and devices, in contrast to implantable, subcutaneous, or leadless medical devices, may have reduced patient compliance, increased detection noise, or reduced detection sensitivity.

Determination of CHF, or risk stratification for CHF, often requires some initial assessment time to establish a baseline level or condition from one or more sensors or physiologic information which to detect deviation from and determine a risk of a heart failure event (HFE), or from which to predict or stratify the risk of the patient experiencing an HFE in a following period. Changes in physiologic information can be aggregated and weighted based on one or more patient-specific stratifiers. However, such changes and risk stratification are often associated with one or more thresholds, for example, having a clinical sensitivity and specificity across a target population with respect to a specific condition (e.g., CHF), etc., and one or more specific time periods, such as daily values, short term averages (e.g., daily values aggregated over a number of days), long term averages (e.g., daily values aggregated over a number of short term periods or a greater number of days (sometimes different days than used for the short term average)), etc.

A multisensor algorithm has been demonstrated to predict CHF events in patients with a high sensitivity and low false positive rate using physiologic information detected from one or more implanted or ambulatory medical devices. The multisensor algorithm can determine a composite CHF parameter using one or more of the following physiologic information: heart sounds (e.g., a first heart sound (S1), a second heart sound (S2), a third heart sound (S3), a fourth heart sound (S4), heart-sounds related time intervals, etc.), thoracic impedance (TI), respiratory rate (RR), rapid shallow breathing index (RSBI), heart rate (HR) (e.g., nighttime HR (nHR)), and activity.

In certain examples, the multisensor algorithm used to determine the composite CHF parameter can be adjusted using a determined patient risk level (e.g., a stratifier). The combination of or weight of respective primary and secondary sensors used to determine the composite CHF parameter can be adjusted using the determined patient risk level. For example, if the determined patient risk level indicates a low risk of worsening CHF, the composite CHF parameter can be determined using the primary sensors (and not the secondary sensors). If the determined patient risk level indicates a medium or high risk of worsening heart failure, the composite CHF parameter can be determined using the primary sensors and a combination of the secondary sensors, depending on the determined patient risk level.

The present inventors have recognized, among other thing, using a study of such multisensor algorithm, that certain physiologic information, or a specific combination of physiologic information from specific sensors, can be used to provide an assessment of discharge readiness for a hospitalized patient (or a patient in treatment, in clinic, or otherwise under the care of a clinician or medical care worker), increasing the effectiveness of existing medical devices. 900 CHF patients with an implanted cardiac resynchronization therapy defibrillator (CRT-D) were studied for up to one year. All hospitalizations of such patients were adjudicated by an independent committee. Hospitalizations with heart failure (HF) as a primary cause (HFH) were identified and classified as complicated if followed by all-cause hospitalization or death within a certain number of days of discharge (e.g., from 15 to 180 days, 30 to 60 days, or one or more other ranges, etc.), and classified as uncomplicated otherwise.

Of the 900 CHF patients monitored, 170 HFH were recorded. 149 HFH were classified under the study (certain classifications using 30-day follow-up values fell outside the window of the study), with 109 classified as uncomplicated, and 40 as complicated. Additional HFHs were excluded if sensor data at admission or discharge was not available. Admission-to-discharge differences for uncomplicated HFHs showed improvements in S3, S1, and RR; no significant change in RSBI and nHR; and a reduction in activity. Admission-to-discharge differences for complicated HFHs showed improvement in TI; no significant change in S3, S1, RR, nHR; worsening RSBI; and a reduction in activity. Despite an improvement in TI, a lack of significant change in S3, S1, and RR, as well as worsening in RSBI identified a group of patients with either early HF readmissions or death. Lower activity at discharge likely reflects hospitalization rather than a physiologic need for reduced activity—and moreover, in certain examples, may be used to determine or confirm hospitalization, for example, if other indications of hospitalization are not received or determined.

Tables 1 and 2 illustrate respective values for different physiologic information corresponding to mean and standard deviation admission and discharge values for uncomplicated HFH in Table 1, and complicated HFH in Table 2.

TABLE 1

Uncomplicated HFH

| Daily value statistic | Sensor | Admission mean | Admission stdev | Discharge mean | Discharge stdev | p | N |
|---|---|---|---|---|---|---|---|
| n/a | HeartLogic Index | 24.60 | 18.13 | 25.31 | 19.21 | 0.54 | 89 |
| 24-h mean | S3, mG | 1.43 | 0.45 | 1.32 | 0.49 | 0.02 | 86 |
| 24-h mean | S1, mG | 1.96 | 0.79 | 2.19 | 0.91 | 0.01 | 92 |
| 24-h mean | Thoracic Impedance, ohms | 40.63 | 9.38 | 44.74 | 9.92 | 0.00 | 94 |
| Day-time mean | Rapid Shallow Breathing Index, rpm/ohm | 12.34 | 4.46 | 12.36 | 4.57 | 0.98 | 94 |
| 24-h mean | Respiratory Rate, rpm | 20.12 | 3.26 | 19.30 | 3.23 | 0.00 | 93 |
| Night-time mean | Night Heart Rate, bpm | 78.82 | 11.60 | 78.17 | 10.83 | 0.52 | 87 |
| 24-h mean | Activity, hours/day | 1.20 | 0.82 | 0.61 | 0.51 | 0.00 | 108 |

TABLE 2

Complicated HFH

| Daily value statistic | Sensor | Admission mean | Admission stdev | Discharge mean | Discharge stdev | p | N |
|---|---|---|---|---|---|---|---|
| n/a | HeartLogic Index | 17.90 | 13.01 | 22.03 | 17.47 | 0.08 | 28 |
| 24-h mean | S3, mG | 1.29 | 0.35 | 1.18 | 0.41 | 0.12 | 24 |
| 24-h mean | S1, mG | 1.99 | 0.62 | 2.16 | 0.66 | 0.17 | 26 |
| 24-h mean | Thoracic Impedance, ohms | 44.22 | 11.04 | 47.40 | 12.31 | 0.01 | 29 |
| Day-time mean | Rapid Shallow Breathing Index, rpm/ohm | 10.39 | 4.23 | 13.19 | 5.15 | 0.01 | 29 |
| 24-h mean | Respiratory Rate, rpm | 20.68 | 3.91 | 20.65 | 3.71 | 0.95 | 31 |
| Night-time mean | Night Heart Rate, bpm | 77.72 | 13.00 | 80.71 | 13.83 | 0.12 | 26 |
| 24-h mean | Activity, hours/day | 1.11 | 0.72 | 0.52 | 0.46 | 0.00 | 38 |

In an example, the present inventors have recognized, using the results of such study, that certain sensor values (e.g., daily, hourly, short or long-term, or one or more other values of one or more specific sensors or physiologic information) prior to admission (e.g., on the day before admission) compared to such certain (or other) sensor values (e.g., daily, hourly, short or long-term, or one or more other values of the one or more specific sensors or physiologic information, or other values of one or more other sensors or physiologic information) before discharge (e.g., on the day before discharge) provided a higher correlation to the classified complicated and uncomplicated HFH.

In an example, a system including one or more ambulatory medical devices can provide a discharge readiness assessment of a monitored patient in an in-hospitalization mode to avoid complicated hospitalizations, thereby reducing power usage of existing ambulatory medical devices during hospitalization, decreasing memory and processor usage or requirements of the system, extending the lifetime of existing ambulatory medical devices, reducing medical costs in the system by avoiding emergency care associated with rehospitalizations, and enabling preventive intervention.

The discharge readiness assessment is in contrast to and different from an indication or alert to seek hospitalization or intervention prior to hospitalization, and also in contrast to and different from a hospital readmission indication or wellness indication post-discharge. For example, whereas thoracic impedance is a driver of many pre-hospitalization and post-discharge indications, as a decrease in thoracic impedance is an indication of fluid accumulation, and an increase in the present inventors have recognized that thoracic impedance is not correlative to a determination of discharge readiness. In another example, indications of patient activity during hospitalization are also not correlative to a determination of discharge readiness. However, heart sounds, such as S3 and S1, and respiration, such as respiratory rate (RR) and rapid shallow breathing index (RSBI) are unexpectedly more correlative to discharge readiness than other physiologic information (e.g., thoracic impedance, activity, etc.).

FIG. 1 illustrates an example system (e.g., a medical device, etc.) 100 including a signal receiver circuit 102 and an assessment circuit 104. The signal receiver circuit 102 can be configured to receive patient information, such as physiologic information of a patient (or group of patients) from one or more sensors. The assessment circuit 104 can be configured to determine an indicator of one or more physiologic conditions or patient wellness using the received physiologic information. For example, the assessment circuit can be configured to determine a worsening heart failure (HF) risk calculation for the patient using the received patient information. The worsening HF risk calculation can include a composite CHF risk indicator determined using a combination of received physiologic information that changes in response to cardiac decompensation, including one or more of a first heart sound, a third heart sound, respiration rate, respiration volume, thoracic impedance, heart rate, or daily patient activity. In certain examples, the individual sensor inputs can be stratified, or one or more sensor weightings can be adjusted depending on the values of one or more other physiologic parameters.

In an example, the signal receiver circuit can be configured to receive an indication of hospitalization of the patient. The indication can include a location-based indication, an alert-based indication, or an indication from the patient, a medical facility, a clinician, medical records, or one or more other care giver or user associated with the patient. Once the indication of hospitalization is received, the assessment circuit 104 can transition from a pre-hospitalization mode to a hospitalization mode, where the assessment circuit 104 can be configured to determine a discharge readiness indicator.

In an example, the discharge readiness indicator can be computed using received physiologic information, such as patient information received from the receiver circuit 102. In certain examples, the assessment circuit 104 can determine the discharge readiness indicator using at least some of the information used to determine the indicator prior to hospitalization (or post-discharge), but differently. For example, the assessment circuit 104 can determine the indicator prior to hospitalization (or post-discharge) using thoracic impedance (TI), and can determine the discharge readiness indicator without using thoracic impedance, or by significantly reducing a weighting of such physiologic information. In other examples, the assessment circuit 104 can determine the indicator prior to hospitalization (or post discharge) using an association between physiologic information, such as thoracic impedance and tidal volume (TV), whereas the assessment circuit 104 can determine the discharge readiness indicator using a disassociation of such physiologic information. For example, an increase in TI is typically associated with a decrease in fluid accumulation; however, in combination with a decrease in TV in a hospitalization setting, the increase in TI and decrease in TV is a negative indicator for discharge readiness.

In an example, the discharge readiness indicator can be determined using a detected change between a current or recent physiologic information or one or more parameters and the same or different physiologic information or one or more parameters at or prior to hospitalization. In certain examples, the specific physiologic information, parameters, weightings, or thresholds can be adjusted or optimized to reduce rehospitalizations (e.g., rehospitalizations within 30 days, 45 days, 60 days, etc.) for the initial condition the patient was admitted for, or for one or more other conditions, including patient overall condition, overall mortality indicator, long- or short-term prognosis, etc.

In an example, the assessment circuit 104 can determine a discharge readiness indicator using respiration information from the patient. The better a patient is breathing (e.g., increased TV, decreased RSBI, etc.), the higher the discharge readiness indicator, indicating that the patient is more likely to have a positive outcome after discharge.

In an example, the assessment circuit 104 can determine a discharge readiness indicator using heart sound information from the patient. For example, a decrease in a detected third heart sound (S3) energy, or an increase in a first heart sound (S1) amplitude or energy, indicate that the patient is more likely to have a positive outcome after discharge.

In other examples, the assessment circuit 104 can determine a discharge readiness indicator using a combination of respiration information and heart sound information, and in certain examples, one or more other information (e.g., a disassociation with thoracic impedance and respiration, etc.). In other examples, the assessment circuit 104 can determine a discharge readiness indicator without using certain information beneficial in pre-hospitalization and post-discharge patient monitoring, such as thoracic impedance or activity.

The assessment circuit 104 can be configured to provide an output to a user, such as to a display or one or more other user interface, the output including an indication of discharge readiness, such as a score, a trend, or other indication.

Figure 2:
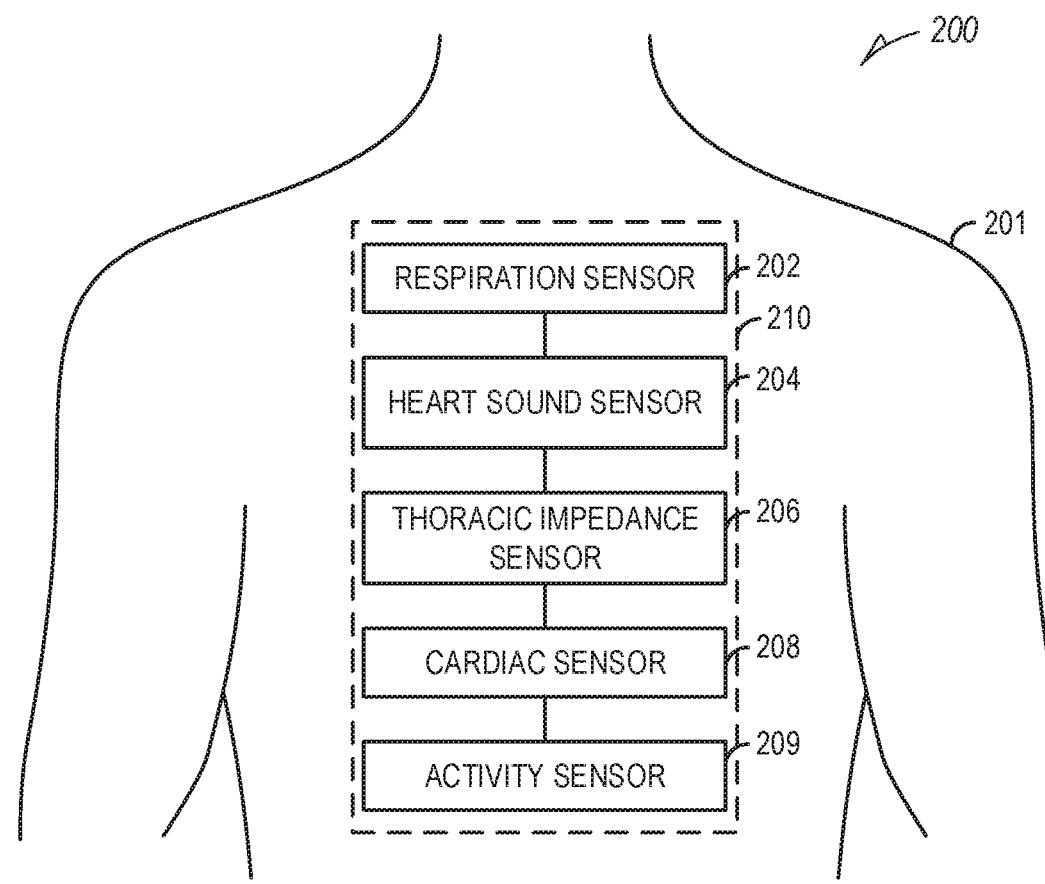
FIG. 2 illustrates an example system including an ambulatory medical device (AMD) configured to sense or detect information from a patient.

FIG. 2 illustrates an example system 200 including an ambulatory medical device (AMD) 210 configured to sense or detect information from a patient 201. In an example, the AMID 210 can include an implantable medical device (IMD), a subcutaneous or leadless medical device, a wearable or external medical device, or one or more other implantable or external medical devices or patient monitors. The AMD 210 can include a single device, or a plurality of medical devices or monitors configured to detect patient information.

The AMD 210 can include a respiration sensor 202 configured to receive respiration information (e.g., a respiration rate (RR), a respiration volume (tidal volume), etc.) of the patient 201, a heart sound sensor 204 configured to receive heart sound information of the patient 201, a thoracic impedance sensor 206 configured to receive impedance information from the patient 201, a cardiac sensor 208 configured to receive cardiac electrical information from the patient 201, and an activity sensor 209 configured to receive information about a physical motion (e.g., activity, posture, etc.) of the patient 201, or one or more other sensors configured to receive physiologic information of the patient 201.

In an example, the sensors in the AMD 210 include existing physiologic sensors. However, using the system and methods described herein, the sensitivity and specificity of one or more metrics associated with a risk of worsening congestive heart failure (CHF) detected using existing sensors can be increased without otherwise increasing system cost or power, or negatively affecting usable battery life of the existing sensors.

Figure 3:
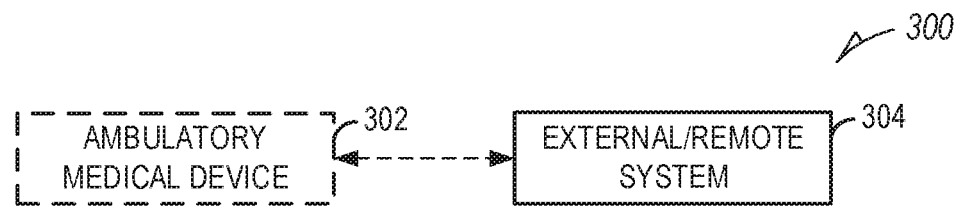
FIG. 3 illustrates an example system including an ambulatory medical device (AMD) coupled to an external or remote system.

FIG. 3 illustrates an example system 300 including an ambulatory medical device (AMD) 302 coupled to an external or remote system 304, such as an external programmer. In an example, the AMD 302 can be an implantable device, an external device, or a combination or permutation of one or more implantable or external devices. In an example, one or more of the signal receiver circuit 102 or the assessment circuit 104 can be located in the AMD 302, or the remote system 304. The remote system 304 can include a specialized device configured to interact with the AMD 302, including to program or receive information from the AMD 302.

In an example, one or more of the AMD 302 or the remote system 304 can be configured to detect a hospitalization event for the patient, either using a location-based detection of an associated patient of the AMD 302 in a hospital, or by receiving an indication, notification, or other input of hospitalization from a user, such as the patient, a clinician, or other caregiver or person associated with a hospital or the remote system 304, or a notification of hospitalization of the patient from medical records.

Figure 4:
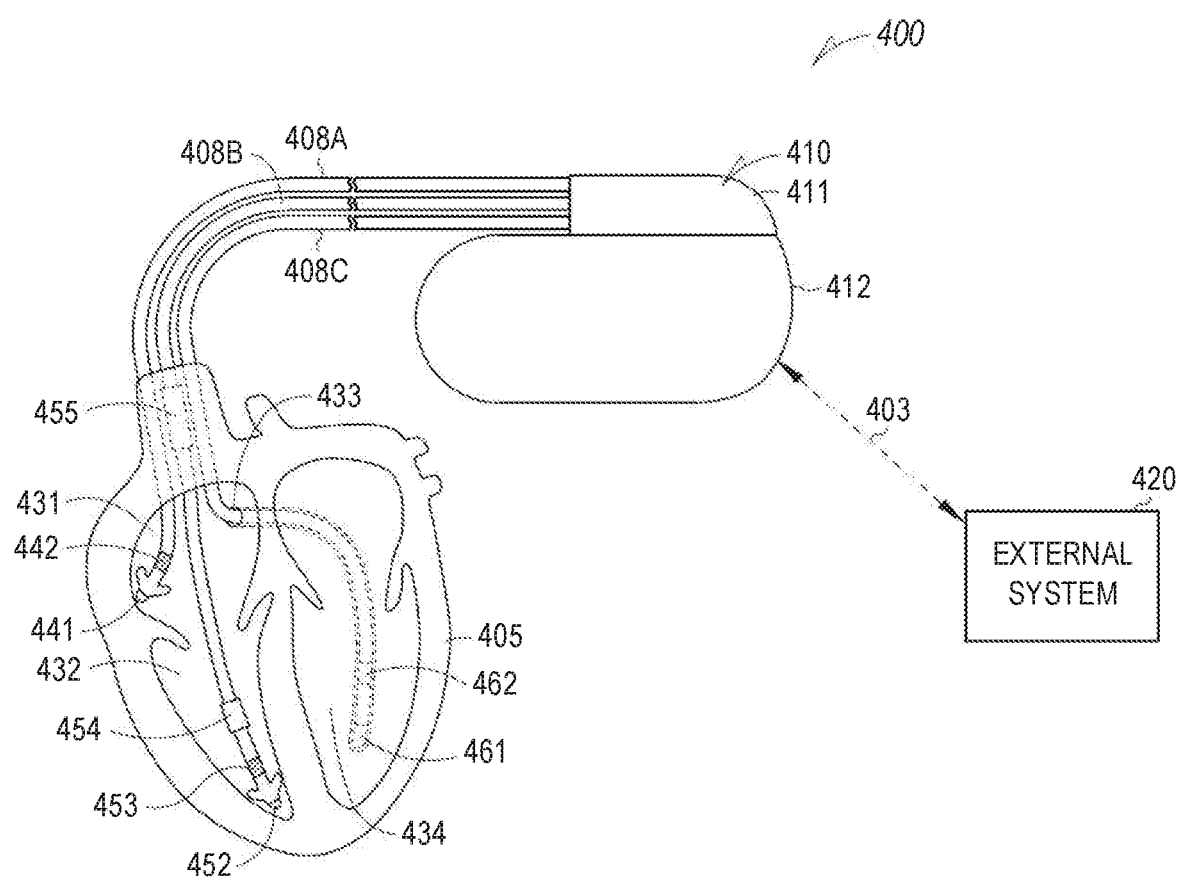
FIG. 4 illustrates an example of a Cardiac Rhythm Management (CRM) system.

FIG. 4 illustrates an example of a Cardiac Rhythm Management (CRM) system 400 and portions of an environment in which the CRM system 400 can operate. The CRM system 400 can include an ambulatory medical device, such as an implantable medical device (IMD) 410 that can be electrically coupled to a heart 405 such as through one or more leads 408A-C coupled to the IMD 410 using a header 411, and an external system 420 that can communicate with the IMD 410 such as via a communication link 403. The IMD 410 may include an implantable cardiac device such as a pacemaker, an implantable cardioverter-defibrillator (ICD), or a cardiac resynchronization therapy defibrillator (CRT-D). The IMD 410 can include one or more monitoring or therapeutic devices such as a subcutaneously implanted device, a wearable external device, a neural stimulator, a drug delivery device, a biological therapy device, or one or more other ambulatory medical devices. The IMD 410 may be coupled to, or may be substituted by a monitoring medical device such as a bedside or other external monitor.

As illustrated in FIG. 4, the IMD 410 can include a hermetically sealed can 412 that can house an electronic circuit that can sense a physiologic signal in the heart 405 and can deliver one or more therapeutic electrical pulses to a target region, such as in the heart, such as through one or more leads 408A-C. In certain examples, the CRM system 400 can include only a single lead, such as 408B, or can include only two leads, such as 408A and 408B.

The lead 408A can include a proximal end that can be configured to be connected to IMD 410 and a distal end that can be configured to be placed at a target location such as in the right atrium (RA) 431 of the heart 405. The lead 408A can have a first pacing-sensing electrode 441 that can be located at or near its distal end, and a second pacing-sensing electrode 442 that can be located at or near the electrode 441. The electrodes 441 and 442 can be electrically connected to the IMD 410 such as via separate conductors in the lead 408A, such as to allow for sensing of the right atrial activity and optional delivery of atrial pacing pulses. The lead 408B can be a defibrillation lead that can include a proximal end that can be connected to IMD 410 and a distal end that can be placed at a target location such as in the right ventricle (RV) 432 of heart 405. The lead 408B can have a first pacing-sensing electrode 452 that can be located at distal end, a second pacing-sensing electrode 453 that can be located near the electrode 452, a first defibrillation coil electrode 454 that can be located near the electrode 453, and a second defibrillation coil electrode 455 that can be located at a distance from the distal end such as for superior vena cava (SVC) placement. The electrodes 452 through 455 can be electrically connected to the IMD 410 such as via separate conductors in the lead 408B. The electrodes 452 and 453 can allow for sensing of a ventricular electrogram and can optionally allow delivery of one or more ventricular pacing pulses, and electrodes 454 and 455 can allow for delivery of one or more ventricular cardioversion/defibrillation pulses. In an example, the lead 408B can include only three electrodes 452, 454 and 455. The electrodes 452 and 454 can be used for sensing or delivery of one or more ventricular pacing pulses, and the electrodes 454 and 455 can be used for delivery of one or more ventricular cardioversion or defibrillation pulses. The lead 408C can include a proximal end that can be connected to the IMD 410 and a distal end that can be configured to be placed at a target location such as in a left ventricle (LV) 434 of the heart 405. The lead 408C may be implanted through the coronary sinus 433 and may be placed in a coronary vein over the LV such as to allow for delivery of one or more pacing pulses to the LV. The lead 408C can include an electrode 461 that can be located at a distal end of the lead 408C and another electrode 462 that can be located near the electrode 461. The electrodes 461 and 462 can be electrically connected to the IMD 410 such as via separate conductors in the lead 408C such as to allow for sensing of the LV electrogram and optionally allow delivery of one or more resynchronization pacing pulses from the LV.

The IMD 410 can include an electronic circuit that can sense a physiologic signal. The physiologic signal can include an electrogram or a signal representing mechanical function of the heart 405. The hermetically sealed can 412 may function as an electrode such as for sensing or pulse delivery. For example, an electrode from one or more of the leads 408A-C may be used together with the can 412 such as for unipolar sensing of an electrogram or for delivering one or more pacing pulses. A defibrillation electrode from the lead 408B may be used together with the can 412 such as for delivering one or more cardioversion/defibrillation pulses. In an example, the IMD 410 can sense impedance such as between electrodes located on one or more of the leads 408A-C or the can 412. The IMD 410 can be configured to inject current between a pair of electrodes, sense the resultant voltage between the same or different pair of electrodes, and determine impedance using Ohm's Law. The impedance can be sensed in a bipolar configuration in which the same pair of electrodes can be used for injecting current and sensing voltage, a tripolar configuration in which the pair of electrodes for current injection and the pair of electrodes for voltage sensing can share a common electrode, or tetrapolar configuration in which the electrodes used for current injection can be distinct from the electrodes used for voltage sensing. In an example, the IMD 410 can be configured to inject current between an electrode on the RV lead 408B and the can 412, and to sense the resultant voltage between the same electrodes or between a different electrode on the RV lead 408B and the can 412. A physiologic signal can be sensed from one or more physiologic sensors that can be integrated within the IMD 410. The IMD 410 can also be configured to sense a physiologic signal from one or more external physiologic sensors or one or more external electrodes that can be coupled to the IMD 410. Examples of the physiologic signal can include one or more of heart rate, heart rate variability, intrathoracic impedance, intracardiac impedance, arterial pressure, pulmonary artery pressure, RV pressure, LV coronary pressure, coronary blood temperature, blood oxygen saturation, one or more heart sounds, physical activity or exertion level, physiologic response to activity, posture, respiration, body weight, or body temperature.

The arrangement and functions of these leads and electrodes are described above by way of example and not by way of limitation. Depending on the need of the patient and the capability of the implantable device, other arrangements and uses of these leads and electrodes are.

The CRM system 400 can include a patient chronic condition-based HF assessment circuit, such as illustrated in the commonly assigned Qi An et al., U.S. Pat. No. 9,622, 664, titled "Methods and Apparatus for Detecting Heart Failure Decompensation Event and Stratifying the Risk of the Same," incorporated herein by reference in its entirety. The patient chronic condition-based HF assessment circuit can include a signal analyzer circuit and a risk stratification circuit. The signal analyzer circuit can receive patient chronic condition indicators and one or more physiologic signals from the patient, and select one or more patient-specific sensor signals or signal metrics from the physiologic signals. The signal analyzer circuit can receive the physiologic signals from the patient using the electrodes on one or more of the leads 408A-C, or physiologic sensors deployed on or within the patient and communicated with the IMD 410. The risk stratification circuit can generate a composite risk index indicative of the probability of the patient later developing an event of worsening of HF (e.g., an HF decompensation event) such as using the selected patient-specific sensor signals or signal metrics. The HF decompensation event can include one or more early precursors of an HF decompensation episode, or an event indicative of HF progression such as recovery or worsening of status.

The external system 420 can allow for programming of the IMD 410 and can receives information about one or more signals acquired by IMD 410, such as can be received via a communication link 403. The external system 420 can include a local external IMD programmer. The external system 420 can include a remote patient management system that can monitor patient status or adjust one or more therapies such as from a remote location.

The communication link 403 can include one or more of an inductive telemetry link, a radio-frequency telemetry link, or a telecommunication link, such as an Internet connection. The communication link 403 can provide for data transmission between the IMD 410 and the external system 420. The transmitted data can include, for example, real-time physiologic data acquired by the 410, physiologic data acquired by and stored in the IMD 410, therapy history data or data indicating IMD operational status stored in the IMD 410, one or more programming instructions to the IMD 410 such as to configure the IMD 410 to perform one or more actions that can include physiologic data acquisition such as using programmably specifiable sensing electrodes and configuration, device self-diagnostic test, or delivery of one or more therapies.

The patient chronic condition-based HF assessment circuit, or other assessment circuit, such as the assessment circuit 104 configured to determine an indication of discharge readiness for the patient, may be implemented at the external system 420, which can be configured to perform HF risk stratification such as using data extracted from the IMD 410 or data stored in a memory within the external system 420. Portions of patient chronic condition-based HF or other assessment circuit may be distributed between the IMD 410 and the external system 420.

Portions of the IMD 410 or the external system 420 can be implemented using hardware, software, or any combination of hardware and software. Portions of the IMD 410 or the external system 420 may be implemented using an application-specific circuit that can be constructed or configured to perform one or more particular functions, or can be implemented using a general-purpose circuit that can be programmed or otherwise configured to perform one or more particular functions. Such a general-purpose circuit can include a microprocessor or a portion thereof a microcontroller or a portion thereof or a programmable logic circuit, or a portion thereof. For example, a "comparator" can include, among other things, an electronic circuit comparator that can be constructed to perform the specific function of a comparison between two signals or the comparator can be implemented as a portion of a general-purpose circuit that can be driven by a code instructing a portion of the general-purpose circuit to perform a comparison between the two signals. While described with reference to the IMD 410, the CRM system 400 could include a subcutaneous medical device (e.g., subcutaneous ICD, subcutaneous diagnostic device), wearable medical devices (e.g., patch based sensing device), or other external medical devices.

Figure 5:
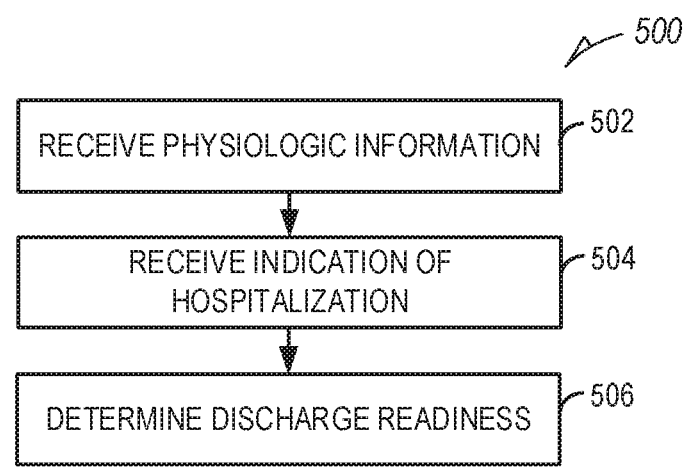
FIG. 5 illustrates an example method of determining an indication of discharge readiness for a patient, such as by computing a discharge readiness score, or composite discharge readiness score, following hospitalization of the patient.

FIG. 5 illustrates an example method of determining an indication of discharge readiness for a patient, such as by computing a discharge readiness score, or composite discharge readiness score, following hospitalization of the patient.

At 502, physiologic information can be received, such as using sensor of an ambulatory medical device (AMD) or a signal receiver circuit of an AMD or a remote system. In certain examples, an hourly, 6-hour, daily, daytime, nighttime, short or long-term values, etc. (or combinations thereof such as a 30-day daytime trend, etc.) of one or more physiologic or composite physiologic parameters can be computed using the received physiologic information. In other examples, the computed physiologic or composite physiologic parameters can be received.

At 504, an indication of hospitalization of the patient can be received. In an example, an AMD can be configured to detect a location of the patient or the AMD, or receive information from the patient, a user, or one or more other machine or process, including a medical record or other input.

At 502, an indication of hospitalization of the patient can be received. In an example, an AMD can be configured to detect a location of the patient or the AMD, or receive information from the patient, a user, or one or more other machine or process, including a medical record or other input.

At 506, an indication of discharge readiness can be determined, such as using a comparison of one or more physiologic or composite physiologic parameter, such as a current daily average value (e.g., if computed at midnight, the current daily value can represent the average value of the prior day) to the daily average value at hospitalization. In an example, a current value compared to or normalized by the value at or prior to hospitalization can be compared to a threshold. In an example, the value can include a composite value of multiple parameters each having an associated weighting. The weighting can depend on, among other things, one or more other physiologic parameter or determination of patient risk.

Figure 6:
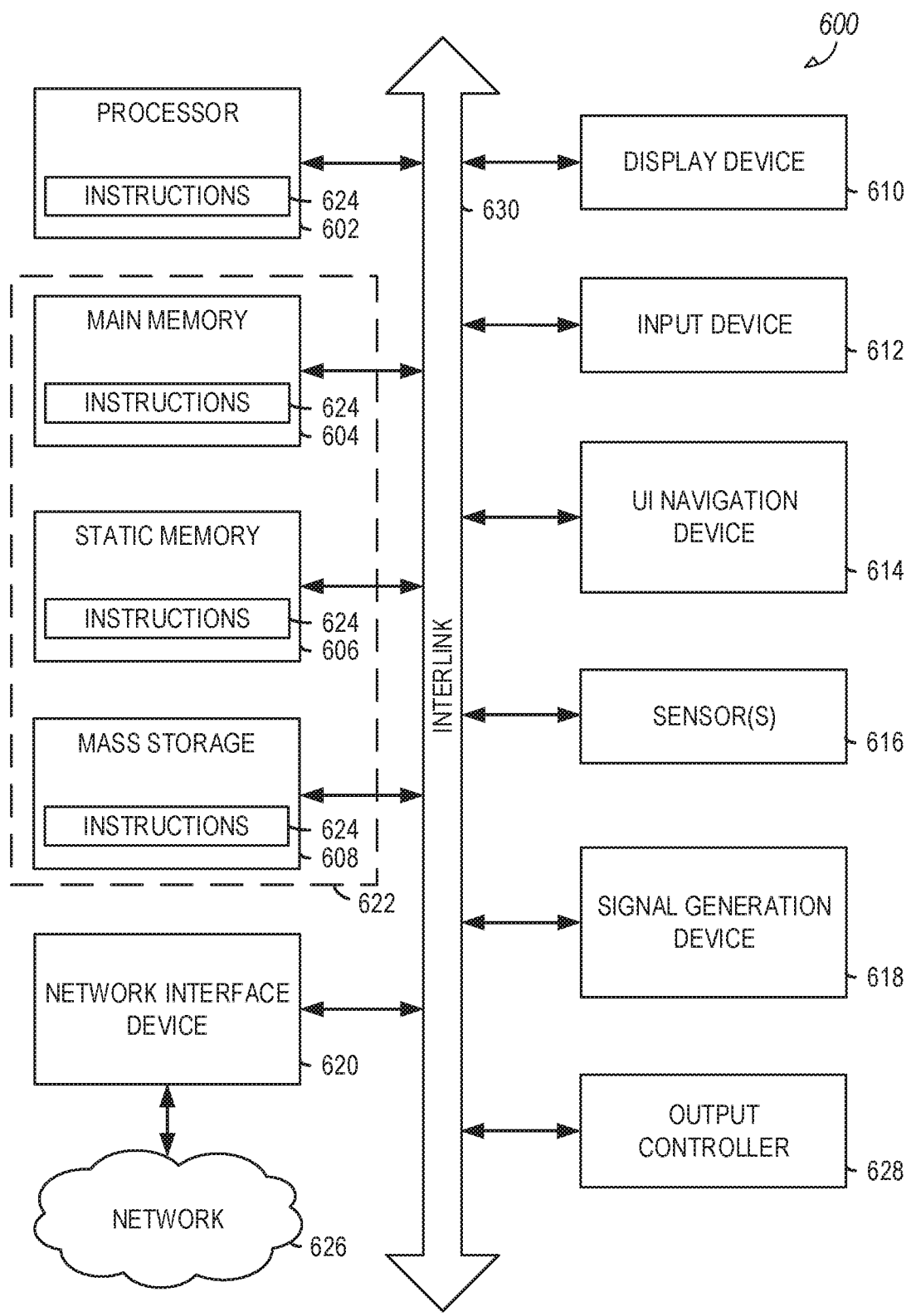
FIG. 6 illustrates a block diagram of an example machine upon which any one or more of the techniques discussed herein may perform.

FIG. 6 illustrates a block diagram of an example machine 600 upon which any one or more of the techniques (e.g., methodologies) discussed herein may perform. Portions of this description may apply to the computing framework of one or more of the medical devices described herein, such as the IMD, the external programmer, etc.

Examples, as described herein, may include, or may operate by, logic or a number of components, or mechanisms in the machine 600. Circuitry (e.g., processing circuitry) is a collection of circuits implemented in tangible entities of the machine 600 that include hardware (e.g., simple circuits, gates, logic, etc.). Circuitry membership may be flexible over time. Circuitries include members that may, alone or in combination, perform specified operations when operating. In an example, hardware of the circuitry may be immutably designed to carry out a specific operation (e.g., hardwired). In an example, the hardware of the circuitry may include variably connected physical components (e.g., execution units, transistors, simple circuits, etc.) including a machine-readable medium physically modified (e.g., magnetically, electrically, movable placement of invariant massed particles, etc.) to encode instructions of the specific operation. In connecting the physical components, the underlying electrical properties of a hardware constituent are changed, for example, from an insulator to a conductor or vice versa. The instructions enable embedded hardware (e.g., the execution units or a loading mechanism) to create members of the circuitry in hardware via the variable connections to carry out portions of the specific operation when in operation. Accordingly, in an example, the machine-readable medium elements are part of the circuitry or are communicatively coupled to the other components of the circuitry when the device is operating. In an example, any of the physical components may be used in more than one member of more than one circuitry. For example, under operation, execution units may be used in a first circuit of a first circuitry at one point in time and reused by a second circuit in the first circuitry, or by a third circuit in a second circuitry at a different time. Additional examples of these components with respect to the machine 600 follow.

In alternative embodiments, the machine 600 may operate as a standalone device or may be connected (e.g., networked) to other machines. In a networked deployment, the machine 600 may operate in the capacity of a server machine, a client machine, or both in server-client network environments. In an example, the machine 600 may act as a peer machine in peer-to-peer (P2P) (or other distributed) network environment. The machine 600 may be a personal computer (PC), a tablet PC, a set-top box (STB), a personal digital assistant (PDA), a mobile telephone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein, such as cloud computing, software as a service (SaaS), other computer cluster configurations.

The machine (e.g., computer system) 600 may include a hardware processor 602 (e.g., a central processing unit (CPU), a graphics processing unit (GPU), a hardware processor core, or any combination thereof), a main memory 604, a static memory (e.g., memory or storage for firmware, microcode, a basic-input-output (BIOS), unified extensible firmware interface (UEFI), etc.) 606, and mass storage 608 (e.g., hard drive, tape drive, flash storage, or other block devices) some or all of which may communicate with each other via an interlink (e.g., bus) 630. The machine 600 may further include a display unit 610, an alphanumeric input device 612 (e.g., a keyboard), and a user interface (UI) navigation device 614 (e.g., a mouse). In an example, the display unit 610, input device 612, and UI navigation device 614 may be a touch screen display. The machine 600 may additionally include a signal generation device 618 (e.g., a speaker), a network interface device 620, and one or more sensors 616, such as a global positioning system (GPS) sensor, compass, accelerometer, or one or more other sensors. The machine 600 may include an output controller 628, such as a serial (e.g., universal serial bus (USB), parallel, or other wired or wireless (e.g., infrared (IR), near field communication (NFC), etc.) connection to communicate or control one or more peripheral devices (e.g., a printer, card reader, etc.).

Registers of the processor 602, the main memory 604, the static memory 606, or the mass storage 608 may be, or include, a machine-readable medium 622 on which is stored one or more sets of data structures or instructions 624 (e.g., software) embodying or utilized by any one or more of the techniques or functions described herein. The instructions 624 may also reside, completely or at least partially, within any of registers of the processor 602, the main memory 604, the static memory 606, or the mass storage 608 during execution thereof by the machine 600. In an example, one or any combination of the hardware processor 602, the main memory 604, the static memory 606, or the mass storage 608 may constitute the machine-readable medium 622. While the machine-readable medium 622 is illustrated as a single medium, the term "machine-readable medium" may include a single medium or multiple media (e.g., a centralized or distributed database, and/or associated caches and servers) configured to store the one or more instructions 624.

The term "machine-readable medium" may include any medium that is capable of storing, encoding, or carrying instructions for execution by the machine 600 and that cause the machine 600 to perform any one or more of the techniques of the present disclosure, or that is capable of storing, encoding or carrying data structures used by or associated with such instructions. Non-limiting machine-readable medium examples may include solid-state memories, optical media, magnetic media, and signals (e.g., radio frequency signals, other photon based signals, sound signals, etc.). In an example, a non-transitory machine-readable medium comprises a machine-readable medium with a plurality of particles having invariant (e.g., rest) mass, and thus are compositions of matter. Accordingly, non-transitory machine-readable media are machine-readable media that do not include transitory propagating signals. Specific examples of non-transitory machine-readable media may include: non-volatile memory, such as semiconductor memory devices (e.g., Electrically Programmable Read-Only Memory (EPROM), Electrically Erasable Programmable Read-Only Memory (EEPROM)) and flash memory devices; magnetic disks, such as internal hard disks and removable disks; magneto-optical disks; and CD-ROM and DVD-ROM disks.

The instructions 624 may be further transmitted or received over a communications network 626 using a transmission medium via the network interface device 620 utilizing any one of a number of transfer protocols (e.g., frame relay, internet protocol (IP), transmission control protocol (TCP), user datagram protocol (UDP), hypertext transfer protocol (HTTP), etc.). Example communication networks may include a local area network (LAN), a wide area network (WAN), a packet data network (e.g., the Internet), mobile telephone networks (e.g., cellular networks), Plain Old Telephone (POTS) networks, and wireless data networks (e.g., Institute of Electrical and Electronics Engineers (IEEE) 802.11 family of standards known as Wi-Fi®, IEEE 802.16 family of standards known as WiMax®), IEEE 802.15.4 family of standards, peer-to-peer (P2P) networks, among others. In an example, the network interface device 620 may include one or more physical jacks (e.g., Ethernet, coaxial, or phone jacks) or one or more antennas to connect to the communications network 626. In an example, the network interface device 620 may include a plurality of antennas to wirelessly communicate using at least one of single-input multiple-output (SIMO), multiple-input multiple-output (MIMO), or multiple-input single-output (MISO) techniques. The term "transmission medium" shall be taken to include any intangible medium that is capable of storing, encoding or carrying instructions for execution by the machine 600, and includes digital or analog communications signals or other intangible medium to facilitate communication of such software. A transmission medium is a machine-readable medium.

Various embodiments are illustrated in the figures above. One or more features from one or more of these embodiments may be combined to form other embodiments. Method examples described herein can be machine or computer-implemented at least in part. Some examples may include a computer-readable medium or machine-readable medium encoded with instructions operable to configure an electronic device or system to perform methods as described in the above examples. An implementation of such methods can include code, such as microcode, assembly language code, a higher-level language code, or the like. Such code can include computer readable instructions for performing various methods. The code can form portions of computer program products. Further, the code can be tangibly stored on one or more volatile or non-volatile computer-readable media during execution or at other times.

The above detailed description is intended to be illustrative, and not restrictive. The scope of the disclosure should, therefore, be determined with references to the appended claims, along with the full scope of equivalents to which such claims are entitled.

What is claimed is:

1. A system, comprising:
a signal receiver circuit configured to:
receive thoracic impedance information of a patient;
receive heart sound information of the patient; and
receive an indication of hospitalization of the patient; and
an assessment circuit configured to:
in a first mode, determine an indication of heart failure (HF) for the patient using the received thoracic impedance information corresponding to a time prior to the time of the received indication of hospitalization of the patient;
upon receiving the indication of hospitalization of the patient, transition to a second mode; and
in the second mode, determine an indication of discharge readiness for the patient using the received heart sound information, and not the received thoracic impedance information, corresponding to a time between the received indication of hospitalization of the patient and the determined indication of discharge readiness for the patient, the time of the determined indication of discharge readiness for the patient later than the time of the received indication of hospitalization of the patient.

2. The system of claim 1, including:
a respiration sensor configured to detect respiration information from the patient and provide a respiration parameter; and
a heart sound sensor configured to detect heart sound information from the patient and provide a heart sound parameter,
wherein the signal receiver circuit is configured to receive the respiration parameter and the heart sound parameter, wherein the heart sound information comprises the heart sound parameter, and
wherein the assessment circuit is configured to determine the indication of discharge readiness for the patient using the received respiration parameter and the received heart sound parameter, each including a parameter corresponding to the time of the received indication of hospitalization of the patient and corresponding to the time of the determined indication of discharge readiness for the patient.

3. The system of claim 2, wherein the respiration parameter includes at least one of a respiratory rate, a tidal volume, or a rapid shallow breathing index (RSBI) of the patient, and
wherein the heart sound parameter includes at least one of a third heart sound (S3) energy or a first heart sound (S1) amplitude or energy.

4. The system of claim 1, wherein the signal receiver circuit is configured to receive respiration information of the patient, and
wherein the assessment circuit is configured to determine the indication of discharge readiness for the patient using a change in a combination of the received heart sound information and the received respiration information corresponding to the time of the received indication of hospitalization and the combination of the received heart sound information and the received respiration information corresponding to the time of the determined indication of discharge readiness for the patient.

5. The system of claim 1, wherein the signal receiver circuit is configured to receive respiration information of the patient, and
wherein the assessment circuit is configured to determine the indication of discharge readiness using the received heart sound information and the received respiration information, and not the received thoracic impedance information.

6. The system of claim 5, including:
a thoracic impedance sensor configured to detect thoracic impedance information from the patient and provide a thoracic impedance parameter,
wherein the signal receiver circuit is configured to receive the thoracic impedance information from the patient including the thoracic impedance parameter.

7. The system of claim 6, wherein the signal receiver circuit is configured to receive an indication of discharge of the patient from a hospital, and
wherein the assessment circuit is configured to:
upon receiving the indication of discharge of the patient from the hospital, transition to a third mode; and
in the third mode, determine a rehospitalization parameter using the received thoracic impedance information corresponding to a time after discharge of the patient, wherein the rehospitalization parameter is different than the indication of discharge readiness.

8. The system of claim 1, wherein the assessment circuit is configured to provide the determined indication of discharge readiness to a display, and
wherein the assessment circuit is configured to determine the indication of discharge readiness for the patient using the received physiologic heart sound information of the patient corresponding to a time after the received indication of hospitalization of the patient but before discharge of the patient from a hospital.

9. The system of claim 1, wherein the received heart sound information of the patient corresponding to the time of the received indication of hospitalization of the patient includes an average daily value of the heart sound information at the time of the received indication of hospitalization of the patient, and
wherein the received heart sound information of the patient corresponding to the time of the determined indication of discharge readiness includes a current average daily value of the heart sound information at the time of the determined indication of discharge readiness, later than the time of the received indication of hospitalization of the patient.

10. The system of claim 1, wherein the assessment circuit is configured to:
determine, at a first time, a first discharge score using the received heart sound information of the patient corresponding to the time of the received indication of hospitalization of the patient; and determine, at a second time later than the first time, a second discharge score using the received heart sound information of the patient corresponding to the time of the determined indication of discharge readiness for the patient, wherein the assessment circuit is configured to determine the indication of discharge readiness for the patient using the determined first and second discharge scores.

11. At least one non-transitory machine-readable medium including instructions that, when performed by a medical device, cause the medical device to:
receive thoracic impedance information of a patient;
receive heart sound information of the patient;
receive an indication of hospitalization of the patient;
in a first mode, determine an indication of heart failure (HF) for the patient using the received thoracic impedance information corresponding to a time prior to the time of the received indication of hospitalization of the patient;
upon receiving the indication of hospitalization of the patient, transition to a second mode; and
in the second mode, determine an indication of discharge readiness for the patient using the received heart sound information, and not the received thoracic impedance information, corresponding to a time between the received indication of hospitalization of the patient and determining the indication of discharge readiness for the patient, the time of determining the indication of discharge readiness for the patient later than the time of the received indication of hospitalization of the patient.

12. The at least one non-transitory machine-readable medium of claim 11, wherein the instructions further comprise:
receive respiration information of the patient, and
wherein to determine the indication of discharge readiness for the patient comprises to determine the indication of discharge readiness for the patient using the received heart sound information and the received respiration information, and not the received thoracic impedance information.

13. The at least one non-transitory machine-readable medium of claim 11, wherein the instructions that, when performed by the medical device, cause the medical device to receive the heart sound information of the patient include instructions to:
receive an average daily value of the heart sound information corresponding to a time of the received indication of hospitalization of the patient, and
receive a current average daily value of the heart sound information at the time of determining the indication of discharge readiness for the patient.

14. The at least one non-transitory machine-readable medium of claim 11, wherein the instructions that, when performed by the medical device, cause the medical device to determine the indication of discharge readiness for the patient include instructions to:
determine, at a first time, a first discharge score using the received heart sound information of the patient corresponding to the time of the received indication of hospitalization of the patient;
determine, at a second time later than the first time, a second discharge score using the received heart sound information of the patient corresponding to the time of determining the indication of discharge readiness for the patient; and determine the indication of discharge readiness for the patient using the determined first and second discharge scores.

15. A method, comprising:
receiving, using a signal receiver circuit, thoracic impedance information of a patient;
receiving, using the signal receiver circuit, heart sound information of the patient;
receiving, using the signal receiver circuit, an indication of hospitalization of the patient;
determining, using an assessment circuit in a first mode, an indication of heart failure (HF) for the patient using the received thoracic impedance information corresponding to a time prior to the time of the received indication of hospitalization of the patient;
transitioning the assessment circuit from the first mode to a second mode upon receiving the indication of hospitalization of the patient; and
determining, using the assessment circuit in the second mode, an indication of discharge readiness for the patient using the received heart sound information, and not the thoracic impedance information, corresponding to a time between the received indication of hospitalization of the patient and determining the indication of discharge readiness for the patient, the time of determining the indication of discharge readiness for the patient later than the time of the received indication of hospitalization of the patient.

16. The method of claim 15, including:
detecting respiration information from the patient and providing a respiration parameter using a respiration sensor; and
detecting heart sound information from the patient and providing a heart sound parameter using a heart sound sensor,
wherein the receiving heart sound information comprises receiving the heart sound parameter,
wherein the method further comprises receiving, using the signal receiver circuit, the respiration parameter, and
wherein the determining the indication of discharge readiness includes using the received heart sound parameter and the received respiration parameter, each including a parameter corresponding to the time of the received indication of hospitalization of the patient and corresponding to the time of the determined indication of discharge readiness for the patient.

17. The method of claim 16, wherein the receiving the respiration parameter includes receiving at least one of a respiratory rate, a tidal volume, or a rapid shallow breathing index (RSBI) of the patient,
wherein the receiving the heart sound parameter includes receiving at least one of a third heart sound (S3) energy or a first heart sound (S1) amplitude or energy, and
wherein the determining the indication of discharge readiness for the patient includes using a change in a combination of the received heart sound parameter and the received respiration parameter corresponding to the time of the received indication of hospitalization and the combination of the received heart sound parameter and the received respiration parameter corresponding to the time of determining the indication of discharge readiness for the patient.

18. The method of claim 15, comprising receiving respiration information of the patient, and
wherein the determining the indication of discharge readiness includes using the received heart sound information and the received respiration information, and not the received thoracic impedance information.

19. The method of claim 15, wherein the determining the indication of discharge readiness includes:
- determining, at a first time, a first discharge score using the received heart sound information of the patient corresponding to the time of the received indication of hospitalization of the patient;
- determining, at a second time later than the first time, a second discharge score using the received heart sound information of the patient corresponding to the time of determining the indication of discharge readiness for the patient; and
- determining the indication of discharge readiness for the patient using the determined first and second discharge scores.

* * * * *